United States Patent
Henttonen et al.

(10) Patent No.: US 7,595,653 B2
(45) Date of Patent: Sep. 29, 2009

(54) PRESSURE TESTING APPARATUS AND METHOD FOR PRESSURE TESTING

(75) Inventors: Vesa Henttonen, Turku (FI); Kari Hannukainen, Turku (FI)

(73) Assignee: Afore Oy, Turku (FI)

( * ) Notice: Subject to any disclaimer, the term of this patent is extended or adjusted under 35 U.S.C. 154(b) by 0 days.

(21) Appl. No.: 11/572,246

(22) PCT Filed: Jul. 20, 2005

(86) PCT No.: PCT/FI2005/000334

§ 371 (c)(1),
(2), (4) Date: Jan. 17, 2007

(87) PCT Pub. No.: WO2006/008337

PCT Pub. Date: Jan. 26, 2006

(65) Prior Publication Data

US 2007/0245808 A1    Oct. 25, 2007

(30) Foreign Application Priority Data

Jul. 21, 2004  (EP) .................................. 04396050
Jul. 21, 2004  (EP) .................................. 04396051

(51) Int. Cl.
  *G01R 31/26*  (2006.01)
(52) U.S. Cl. ................................... 324/765
(58) Field of Classification Search ......... 324/754–765, 324/156–157
  See application file for complete search history.

(56) References Cited

U.S. PATENT DOCUMENTS

| | | | | |
|---|---|---|---|---|
| 4,777,716 A | * | 10/1988 | Folk et al. ..................... | 29/593 |
| 5,346,513 A | * | 9/1994 | Taniguchi et al. ........... | 29/25.01 |
| 5,668,305 A | * | 9/1997 | Chi et al. ....................... | 73/37 |
| 5,677,477 A | | 10/1997 | Man et al. | |
| 6,373,271 B1 | | 4/2002 | Miller et al. | |
| 6,867,608 B2 | * | 3/2005 | Richmond et al. .......... | 324/754 |
| 2003/0151421 A1 | * | 8/2003 | Leedy ......................... | 324/760 |
| 2003/0153088 A1 | * | 8/2003 | DiMeo, Jr. et al. .......... | 436/113 |
| 2004/0020438 A1 | | 2/2004 | Rechav et al. | |
| 2005/0035311 A1 | * | 2/2005 | Asakawa et al. ........ | 250/559.16 |

FOREIGN PATENT DOCUMENTS

| | | |
|---|---|---|
| JP | 7-35815 A | 2/1995 |
| JP | 08008152 A1 | 1/1996 |
| JP | 2004-325385 A | 11/2004 |
| WO | 2006/008337 A1 | 1/2006 |

OTHER PUBLICATIONS

English translation of Abstract in JP 2004-325385.
English translation of Abstract in JP 7-35815.
Search Report issued in EU App. No. 04396051.7.

* cited by examiner

*Primary Examiner*—Ha Tran T Nguyen
*Assistant Examiner*—Shaun Campbell
(74) *Attorney, Agent, or Firm*—Stiennon & Stiennon

(57) ABSTRACT

A pressure testing apparatus for chips on a wafer has a pressure chamber, a support plate arranged between the upper and lower parts of the housing, a wafer chuck, a testing device and a positioning device. The wafer chuck, the testing device and the positioning device are supported to the support plate and arranged inside the pressure chamber. The support plate has, inside the pressure chamber, an opening providing a gas connection between the upper and lower parts of the housing.

20 Claims, 4 Drawing Sheets

PRESSURE TESTING APPARATUS AND METHOD FOR PRESSURE TESTING

CROSS REFERENCES TO RELATED APPLICATIONS

This application is a U.S. national stage application of International App. No. PCT/FI2005/000334, filed Jul. 20, 2005, the disclosure of which is incorporated by reference herein, and which claims priority on EP App. No. 04396051.7, filed Jul. 21, 2004, and EP App. No. 04396050.9, filed Jul. 21, 2004, the disclosures of which are incorporated by reference herein.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The invention concerns a pressure testing apparatus, a method for pressure testing chips on a wafer and use of such apparatuses.

Pressure sensors are micromechanical devices, which are fabricated in a wafer, typically from 100 to 300 mm in diameter and from 200 to 500 µm in thickness. The wafer is mounted in a test fixture so that the performance of the each individual pressure sensors can be tested. FIG. 1 shows a wafer. The pressure sensors, referred to as chips in the following text, are tested while still in wafer form or after separation from each other (by dicing), using an automatic testing apparatus.

The testing apparatus typically comprises a chuck for the wafer or the test fixture, a card support for a probe card and a positioning device for positioning the wafer or the test fixture during testing. Most of such testing apparatuses function at normal air pressure. However, for pressure sensors, testing at normal air pressure is insufficient. Therefore pressure sensors should be tested at low pressure and/or at overpressure.

In pressure sensor testing, low pressure may be applied towards the lower surface of the wafer so that the low pressure is produced through the chuck. For proper function, the contact surfaces of the sensor should be located on the opposite side of the active pressure surface in the sensor.

Producing overpressure through the chuck is possible, but then the wafer should be held against the chuck using a force at least equal to the force of pressure below the wafer. Since wafers are typically very thin, breaking of the wafer already at very low overpressure is possible.

For overpressure testing, the active pressure surface and its contacts may be located on the same side of the wafer. In a known technique, a conduit in association with the probes of the probe card, for example needles, is brought near the surface of the sensor. Controlling exactly the flow of blowing, a specific area on the wafer, for example a pressure sensor, is pressurized. However, with flow control it is difficult to obtain an exact pressure. Furthermore, by using such known technique it is difficult to achieve a high pressure of over 10 bars.

Another known technique is to force a conduit closely against the surface of the wafer so that the conduit forms a pressure chamber together with the wafer surface. Thus, pressure control is easier. However, in most cases no high contact force is allowed to be directed toward the wafer surface.

In U.S. Pat. No. 4,777,716 a chuck is provided with a seal circumferentially around the wafer. The probe card is located above the chuck below the cover. A pressure sensor to be tested is placed in contact with the probes by moving the chuck upward against the structure above it. Thereby, the chuck becomes tightened against the upper structure and forms a hermetically sealed chamber together with the upper structure. The level of pressure can be varied with aid of an external pressure system. If testing is desired to be done with a great overpressure the pressure force is encountered due to large pressurized area which force tend to open the chamber during testing. The pressure force is directed towards the positioning device of the chuck. Thereby the positioning device should be made heavy by its construction. Another problem is that the force between the sensor and the probes of the probe card cannot be adjusted by the vertical movement of the chuck. Furthermore, the capacity for testing is reduced by the structure of the apparatus. For positioning from one sensor to another sensor, the pressure chamber of the apparatus has to be opened. After closing the chamber it has to be pressurized again.

U.S. Pat. No. 6,373,271 presents another typical solution wherein the above mentioned problems are decreased so that the part of the chuck, which is tightened against the upper structure, is flexible allowing the horizontal movements of the chuck within the specific limits. Thus, opening of a hermetically sealed pressurized chamber between the movements is not required. Flexible construction enables adjustment of applied force between the sensor and the probes of the probe card since the vertical movement is not totally fixed. However, a disadvantage is the great pressure force, which is applied towards the wafer chuck.

One known technique is shown in FIG. 3. The positioning device for the testing apparatus is arranged inside a cylindrical pressure chamber. The pressure chamber experiences a movement due to a change in an applied pressure in the chamber and this movement is conducted to the positioning device through the walls unless the thickness of the wall is well oversized. Thus, the positioning device cannot be fastened rigidly to the walls of the pressure chamber otherwise the movement may cause problems in its positioning accuracy.

SUMMARY OF THE INVENTION

It is therefore an object of the invention to provide a pressure testing apparatus that overcomes the above deficiencies.

Furthermore, an object of the invention is to provide a method for pressure testing chips on a wafer in a pressure chamber and a pressure testing apparatus, which can be utilized at low pressure and/or at overpressure testing of such chips.

Furthermore, an object of the invention is to provide a method for pressure testing separated (diced) chips in a test fixture in a pressure chamber, and a pressure testing apparatus, which can be utilized at low pressure and/or at overpressure testing of such chips.

Typical pressure testing apparatus according to the invention comprises a pressure chamber, which pressure chamber comprises a housing and a loading means for transporting the wafer through the housing into and out from the pressure chamber, the housing comprising an upper part and a lower part. Typical pressure testing apparatus comprises further a support plate arranged between the upper and lower parts of the housing, a wafer chuck, a testing means for testing chips, and a positioning device for positioning the chuck and the chips relative to the testing means.

With the testing means is meant for example probes and a probe card to control measuring in the pressure testing apparatus and a card support to support the probe card. With chips is meant for example pressure sensors, gas sensors or circuits on a wafer or in a test fixture. The chips are sometimes referred to as die. In the following text, the wafer may correspond to the test fixture for the chips although not specifically mentioned. With the test fixture is meant for example a plate comprising a place for the each individual chips. The test fixture may be for example a metal lattice, a frame or a waffle-type carrier. Furthermore, the test fixture may be accomplished by substrate material to which the chips are attached, glued or bonded. The wafer may be for example made of glass or semiconducting material, such as silicon or gallium arsenide.

In typical pressure testing apparatus according to the invention the wafer chuck, the testing means and the positioning device are supported to the support plate and arranged inside the pressure chamber, and furthermore the support plate comprises inside the pressure chamber an opening providing a gas connection between the upper and lower parts of the housing.

In typical pressure testing apparatus, the purpose of the opening is to provide same pressure into the lower part and the upper part of the housing. This way same pressure is applied on both sides of the support plate. The forces towards the upper part of the support plate are likely to be compensated with forces towards the lower part. Thus, the support plate is not bent due to the applied pressure. Furthermore, the structure of the pressure chamber of the pressure testing apparatus enables the use of relatively thin support plate, since the moving force is exerted to the positioning device, the wafer chuck and the testing means only in the planar direction of the support plate. Although the movement of the housing due to changes in applied pressure may cause the positioning device and the wafer chuck to be moved to some extent, the effect of the movement is less than in the case where the positioning device is supported directly to the wall of the housing, as is presented in prior art techniques. In other words, the movement from the housing of the pressure chamber is attenuated by the support plate. Since a wafer or a test fixture containing chips to be tested lies in the wafer chuck, which is supported to the support plate as well as the testing means is supported to the support plate, it becomes possible to improve the accuracy of the positioning device in the pressure testing apparatus.

In a further embodiment of the invention, the support plate is arranged to cover a collar around the periphery of the pressure chamber. The size of the collar depends on the size of the support plate. The width/length of the support plate may be around 1000 millimeters. The outer diameters of the upper and lower parts may be 500-700 millimeters. Thereby the width of the collar around the said periphery may be 150-250 millimeters.

In another further embodiment of the invention the support plate extends from inside of the housing of the pressure chamber to a distance outside of the housing of the pressure chamber. Since the support plate is provided with an opening inside the pressure chamber, the distance extends beginning from the edge of the opening to outside the housing. Thus, the distance may be 300-700 millimeters depending on the size of the support plate and the diameter of the opening.

In another further embodiment of the invention, the support plate is arranged to divide the housing of the pressure chamber into an upper part and a lower part. The upper part may be similar than the lower part or they can be dissimilar. The upper and lower parts and the support plate are however arranged to form a hermetically sealed pressure chamber.

In another further embodiment of the invention the upper part and the lower part are separate parts, which are supported to the support plate. The upper part of the housing is supported to the upper side of the support plate. The upper part provides an upper chamber, which chamber extends above the positioning device and the support plate. Thus, the loading means and the wafer chuck may be arranged in the upper part. Furthermore, the loading means is preferably arranged nearby the wafer chuck. The lower part of the housing is supported to the lower side of the support plate. The lower part provides a lower chamber, which lower chamber extends below the positioning device and the support plate. The positioning device is thus arranged between the upper chamber and the lower chamber.

The pressure is same inside said chambers since the opening provides a gas connection through the support plate. Thus, the pressure forces towards the upper side of the support plate from the upper chamber are to be compensated by the pressure forces towards the lower side of the support plate from the lower chamber.

In another further embodiment of the invention the opening covers a part from the support plate inside the pressure chamber. The opening is then entirely inside the pressure chamber. Furthermore, the support plate may be continuous around the opening. The diameter of the opening is for example 2.5, 5, 10, 15, 20, 30, 40 or 50 percent smaller than the inner diameter $d_1$ of the housing shown in FIG. 6. The diameter of the opening may be for example 15, 30, 60, 90, 120, 180, 240 or 300 mm smaller than the inner diameter $d_1$. Therefore, the diameter of the opening is smaller than the inner diameter of the housing. Thus, the area of the opening of the support plate inside the pressure chamber is smaller than the area of the support plate inside the pressure chamber which area is defined by the housing and includes also the area of the opening.

In another further embodiment of the invention the testing means comprises a probe card. The probe card is provided with contact probes by means of which a singular chip or several chips on a wafer may be tested.

In another further embodiment of the invention the testing means comprises a card support arranged to support the probe card. The card support may be supported directly to the support plate or to the positioning device arranged in the support plate.

In another further embodiment of the invention the pressure testing apparatus comprises a vision system supported to the support plate. Such system may comprise a camera, a microscope and/or a light source.

In another further embodiment of the invention the pressure testing apparatus comprises a window arranged in the housing of the pressure chamber. The window or windows may be then arranged below the vision system if the vision system is arranged outside the pressure chamber. Both the vision system and the windows may be arranged above the upper part of the housing.

The invention concerns furthermore a method for pressure testing chips on a wafer in a pressure chamber, the pressure chamber comprising a housing and a loading means for transporting the wafer through the housing into and out from the pressure chamber, the housing comprising an upper part and lower part, the method comprising, inserting a wafer into a wafer chuck, positioning the wafer chuck relative to a testing means with a positioning device, supporting a testing means by a support plate, changing pressure inside the housing of the pressure chamber, moving the housing of the pressure chamber due to the pressure change and testing the chips on the wafer in the pressure chamber with the testing means.

In a typical method according to the invention, the method comprises supporting the wafer chuck and the positioning device by the support plate, arranging the testing means and the positioning device inside the housing of the pressure chamber, providing an opening and thereby a gas connection through the support plate between the upper chamber and the lower chamber, supporting the upper part of the housing to the upper side of the support plate, thus providing an upper chamber, supporting the lower part of the housing to the lower side of the support plate, thus providing a lower chamber applying equal pressure against the upper and lower surface of the support plate.

In a further embodiment of the invention the method comprises exerting moving force caused by the movement of the housing of the pressure chamber due to the pressure change to the wafer chuck, the testing means and the positioning device only via the support plate.

The invention further relates to the use of a pressure testing apparatus according to present invention for chips on a wafer. For example testing sensors of poisonous gases, for example chemical war gases, can be done safely and effectively.

The details and embodiments described above in connection with the pressure testing apparatus also apply to the present method.

The invention will now be described by way of examples only with reference to accompanying schematical drawings.

DESCRIPTION OF THE PREFERRED EMBODIMENTS

Figure 1:
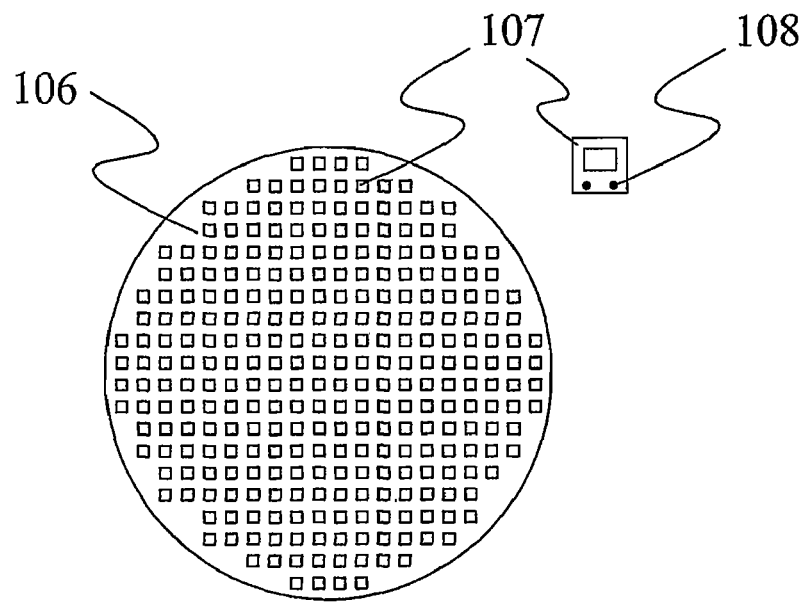
FIG. 1 shows a top view of a wafer that includes chips to be tested.

FIG. 1 shows a top view of a wafer that includes chips to be tested. The wafer 106 contains chips 107, such as pressure sensors. The wafer 106 may contain from 100 to 1000 chips. Furthermore, the chip 107 comprises contact pads 108.

Figure 2:
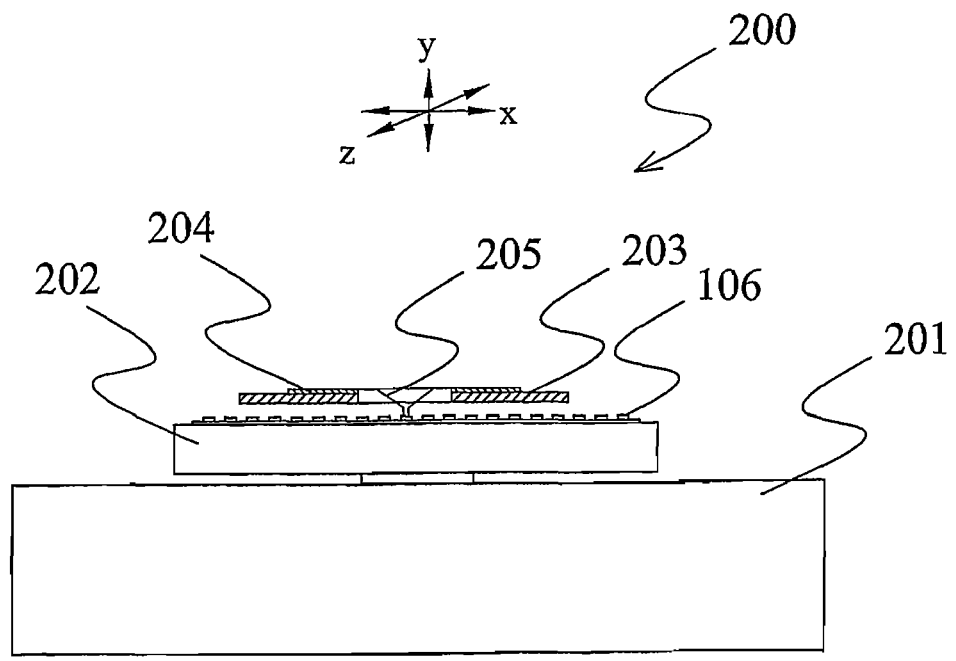
FIG. 2 shows a cross-sectional view of a testing apparatus according to prior art.

FIG. 2 is a cross-sectional view of a testing apparatus according to prior art. It should be noted that the testing apparatus might not be necessarily applied for pressure testing chips without a pressure chamber. The testing apparatus 200 consists of a positioning device 201, a chuck 202 and testing means such as a probe card 204, probes 205 and a card support 203. The positioning device 201 for positioning the chuck 202 is arranged so that the chuck can be moved along the x-, y- and z-axes of the Cartesian coordinate system as is shown by arrows as is shown in FIG. 2. The probe card 204 and its probes 205 are arranged in the card support 203 above the wafer chuck 202.

For testing a chip, the wafer 106 is inserted into the wafer chuck 202 and fastened on it in a manner well known in the art and which will not be described herein. The wafer chuck 202 is moved into a position of device under test or a chip by the positioning device 201 so that the probes 205 can be placed in contact with the contact pads of the chip. The probes 205 of the probe card 204 are forced against the contact pads of the chip 107 and measurements are executed at normal air pressure by the testing means.

Figure 3:
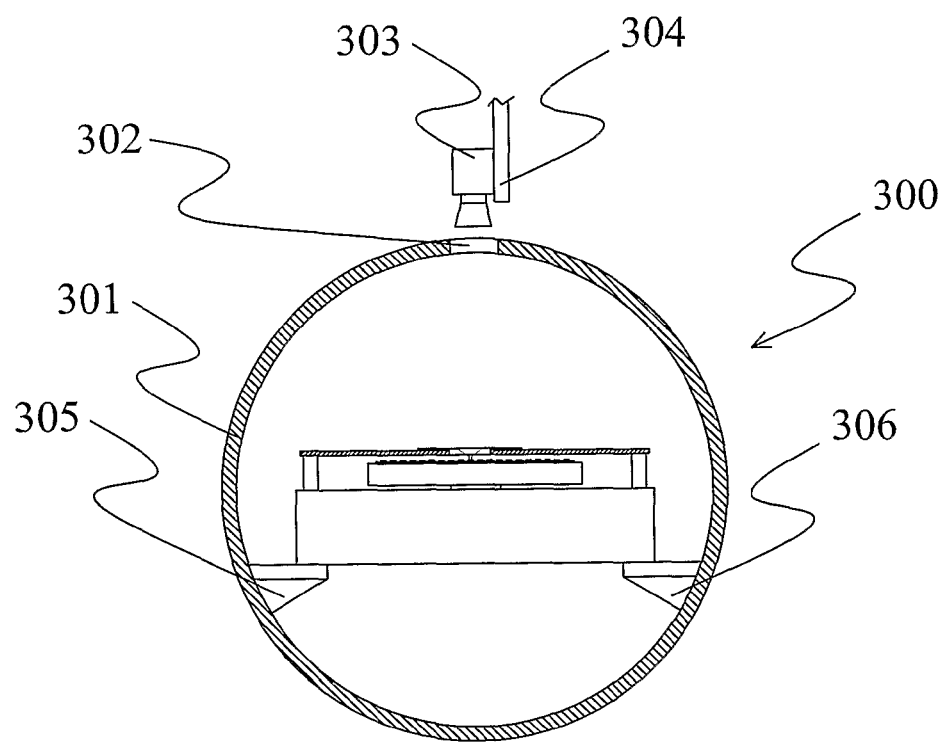
FIG. 3 shows a cross-sectional view of a pressure testing apparatus according to prior art.

Referring to FIG. 3, a cross-sectional view of a pressure testing apparatus according to prior art is shown. The pressure testing apparatus 300 may be partially analogous with the testing apparatus 200 shown in FIG. 2. The pressure testing apparatus comprises a cylindrical pressure chamber 301 provided with a window 302 and a camera 303. The positioning device is mounted to the inner walls of the housing of the pressure chamber by rails 305 and 306. The camera is positioned outside the pressure chamber in a rack 304.

At overpressure, the pressure tends to direct the force towards the walls of the pressure chamber thus pushing the opposite walls and the rails 305, 306 apart. The movement is conducted to the positioning device through the walls unless the thickness of the wall is well oversized. The pressure chamber 301 may expand freely since there is no support arranged outside the housing of the pressure chamber, by which the expansion could be attenuated. Thus, the positioning device is moved undesirably during testing and its accuracy is degraded.

Figure 4:
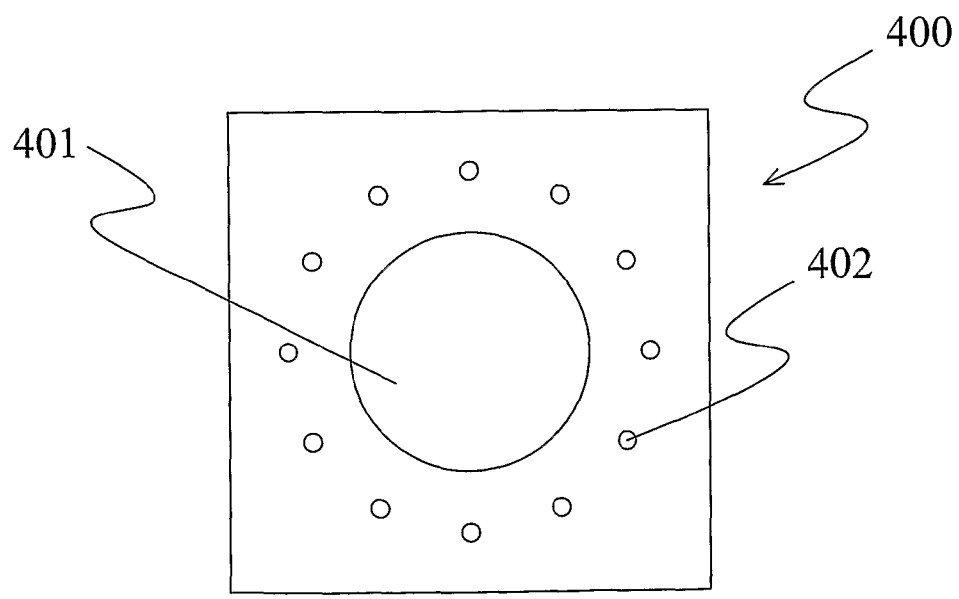
FIG. 4 shows a top view of a support plate according to a first embodiment of the invention presented in FIG. 5.
Figure 5:
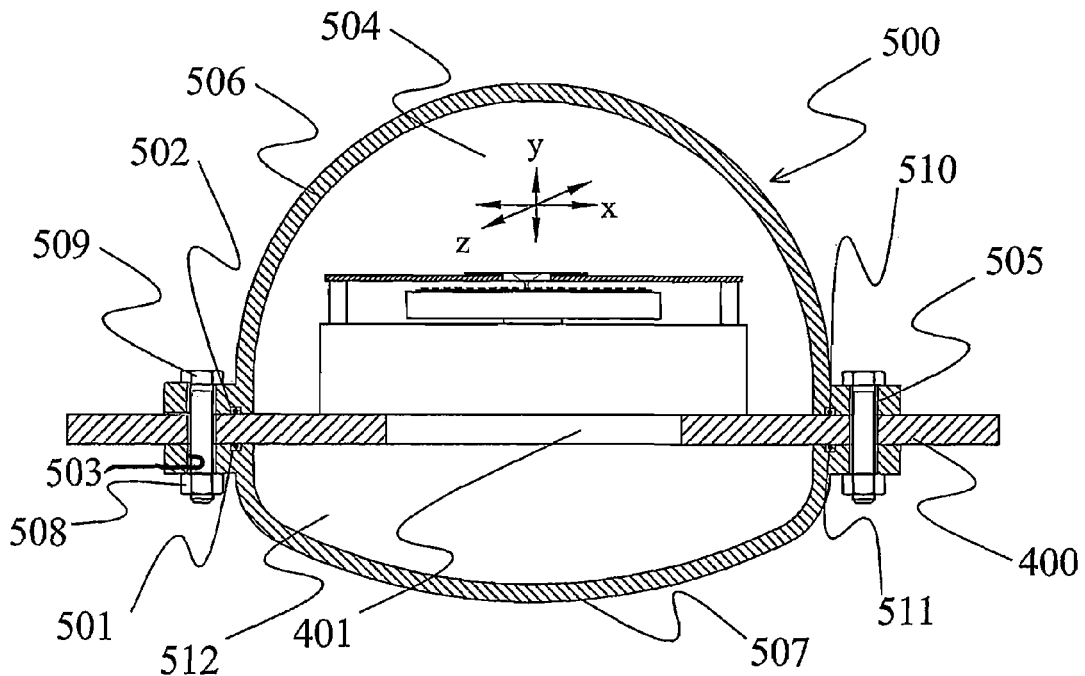
FIG. 5 shows a cross-sectional view of a pressure testing apparatus according to a first embodiment of the invention.

FIG. 4 shows a top view of a support plate according to a first embodiment of the invention presented in FIG. 5. The support plate 400 contains holes 402, which are circumferentially positioned around the opening 401. The opening 401 is entirely inside the continuous support plate 400. The shape of the opening may vary. For example, the opening may be rectangular in shape. In FIG. 4, the opening is circular and arranged inside the periphery of the holes 402. The radius of the opening 401 is chosen so that the positioning device can be supported from the edges of the opening inside the periphery of the holes by the support plate. The radius is around 100-400 millimeters depending on the size of the support plate.

FIG. 5 shows a cross-sectional view of a pressure testing apparatus according to a first embodiment of the invention. The pressure testing apparatus 500 comprises a housing of a pressure chamber provided with an upper part 506 and a lower part 507 and a support plate. The pressure testing apparatus further comprises a testing means, such as probe cards and probes and a card support, a wafer chuck for holding the chips, a positioning device for positioning the wafer chuck and the chips relative to the testing means, as is shown more detailed in FIG. 2. The upper part of the housing is mounted to the upper side of the support plate, thus providing an upper chamber 504. The lower part of the housing is mounted to the lower side of the support plate, thus providing a lower chamber 512. Further, the pressure testing apparatus 500 comprises sealed lead-throughs (not shown) for the electrical cables from the probes and the probe card as well as the positioning device. The pressure testing apparatus is also provided with sealed lead-throughs and ducts for the external pumping system (not shown).

Referring further to FIG. 5, the upper part 506 of the housing of the pressure chamber is provided with a groove 502 and holes 505. An O-ring seal 510 is arranged in the groove 502. The lower part 507 of the housing of the pressure chamber is provided with a groove 501 and holes 503. Furthermore, the lower part 507 is equipped with an O-ring seal 511. Grooves 501 and 502 and seals 510 and 511 are arranged opposite each other on both sides of the support plate.

In FIG. 5, the card support is arranged in the positioning device above the chuck. Alternatively the card support may be arranged in the support plate 400 inside the pressure chamber. The upper part 506 and the lower part 507 are fastened to the support plate 400 by fastening means, for example by bolts 509 and nuts 508, through the holes 503, 505, 402, as is shown in FIGS. 4 and 5. The upper part 506 and the lower part 507 are adapted so that the surfaces with grooves 501, 502 are positioned against the support plate 400. The support plate 400 is arranged horizontally between the upper part 506 and the lower part 507 of the housing of the pressure chamber. Thereby the support plate 400, the upper part 506 and the lower part 507 confine a hermetically sealed chamber.

The diameters of holes 503, 505, 402 are slightly larger than the diameter of bolts 509. Thus, the bolts fasten the upper part firmly to the lower part but allow limited movement of the housing in relation to the support plate. This way the movement of the housing stresses less the support plate and thus makes it possible to use thinner support plates. For example, the thickness of the support plate is around 20 millimeters. The material of the support plate is for example stainless steel.

The width/length of the collar of the support plate is significantly greater than is required by the applied pressure in the pressure chamber. The width/length of the collar of the support plate is for example three, four, five or even ten times greater than is required by the applied pressure in the pressure chamber.

Figure 6:
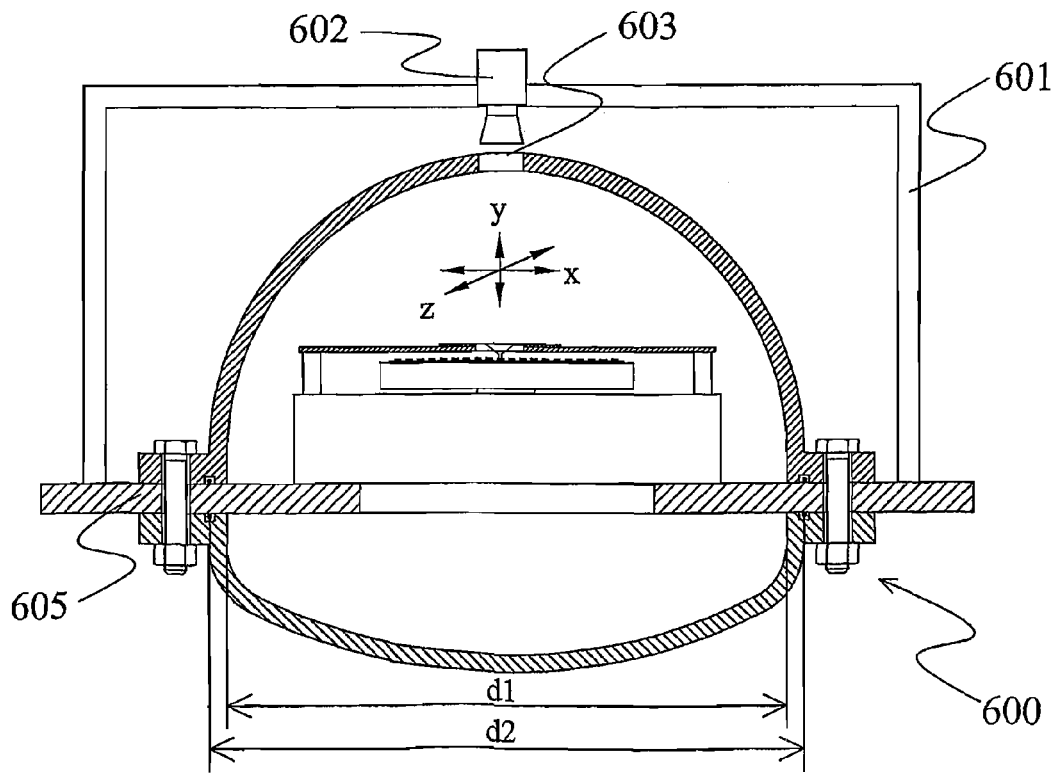
FIG. 6 shows a cross-sectional view of a pressure testing apparatus according to a second embodiment of the invention.

Referring to FIG. 6, a cross-sectional view of a pressure testing apparatus according to a second embodiment of the invention is shown. A support plate 605 is extended to a distance away from outer edges of the housing of the upper part and/or the lower part. Arranged in the support plate 605 is a standing support 601 for a camera 602. The pressure testing apparatus comprises the camera, which is placed on the standing support above the upper part. The upper part of the pressure apparatus is provided with a window 603, which is positioned above the wafer chuck.

In the example of the FIG. 6, areas delimited by the seals and against the upper and lower surfaces of the support plate are equal. The seals are circular in shape and their diameters d2 are equal. That is the seals are equal in size. The seals are circumferentially arranged around the upper and the lower parts of the housing. Furthermore, the inner diameter d1 of the open surface of the upper part of the housing towards the support plate is equal to the inner diameter of the open surface of the lower part towards the support plate. For example d1 is around 600 millimeters and d2 is around 650 millimeters. Thus the diameter of the opening may be around 400 millimeters.

In order to test chips the pressure chamber is opened by loosening the nuts and bolts, and the wafer is inserted into the wafer chuck inside the housing of the pressure chamber. The wafer is fastened on the wafer chuck in a manner well known to those skilled in the art. The pressure chamber is hermetically closed by tightening the nuts and bolts. The test is carried out either at low pressure or at overpressure. The pressure is drawn in the pressure chamber by an external pressure system, for example by mechanical pumping and/or cryogenic pumping. For pressure testing, the wafer is moved by the positioning device in a desired position and the probes are placed in contact with the contact pads of the chip, for example a pressure sensor. The wafer chuck is positioned desirably along x-, y- and z-axes of Cartesian coordinate system as shown in FIG. 6. The chip is tested by the testing means inside the housing of the pressure chamber. When the test is completed the pressure is returned to normal air pressure, for example by opening the air valves arranged in the pressure chamber (not shown).

Figure 7:
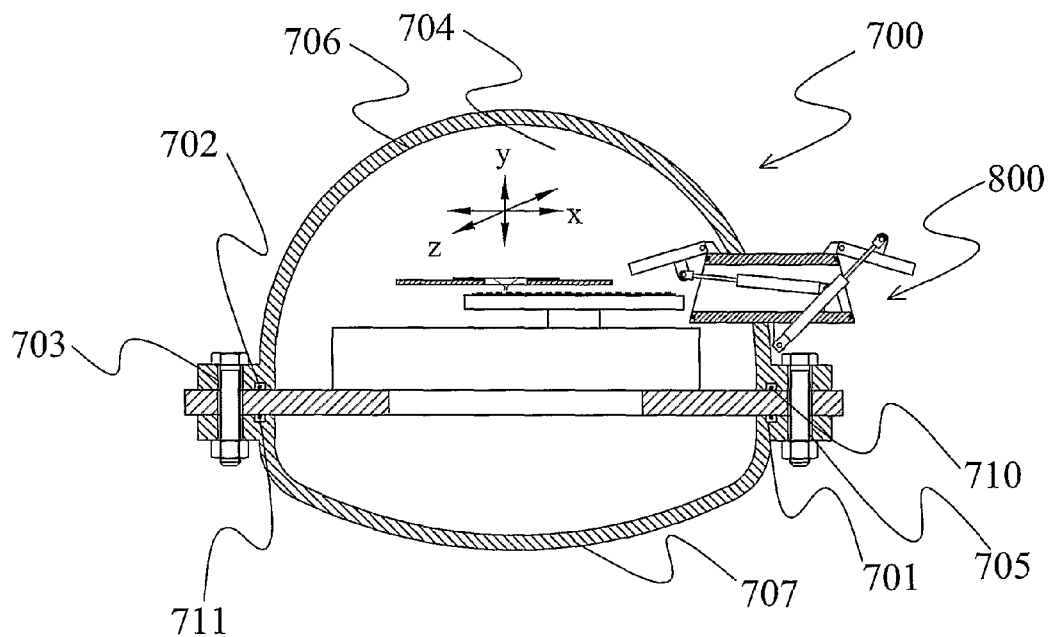
FIG. 7 shows a cross-sectional view of a pressure testing apparatus according to a third embodiment of the invention.

FIG. 7 is a cross-sectional view of a pressure testing apparatus according to a third embodiment of the invention. The upper part of the housing of the pressure chamber comprises a loading means 800, shown detailed in FIG. 8. In this third embodiment, the loading means 800 is positioned in such a manner that the inner opening is inside the pressure chamber. Further, the pressure testing apparatus 700 comprises sealed lead-throughs (not shown) for the electrical cables from the testing means and the positioning device. The pressure testing apparatus 700 is also provided with sealed lead-throughs, flanges and ducts for an external pumping system (not shown). The upper part 706 of the housing is provided with a groove 702 and holes 703. An O-ring seal 710 is arranged in the groove 702. Further, the lower part 707 of the housing is provided with a groove 701 and holes 705. The groove 701 is equipped with an O-ring seal 711.

Figure 8:
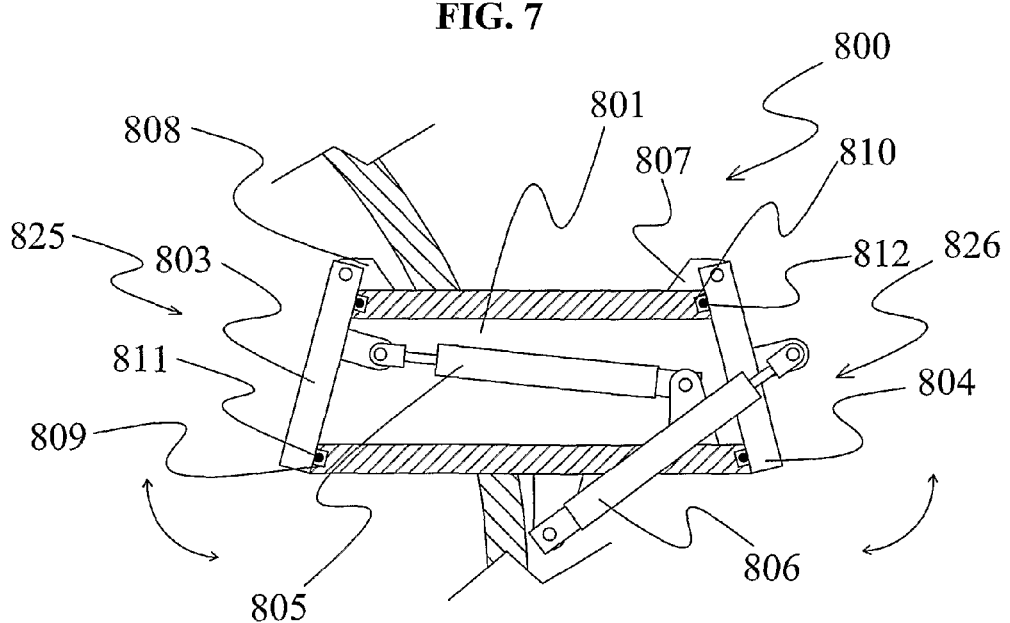
FIG. 8 shows a cross-sectional view of a loading means according to a third embodiment of the invention.

Referring to FIG. 8, a cross-sectional view of a loading means according to the third embodiment of the invention is shown. The purpose of the loading means is to transport the wafer through the housing into and out from the pressure chamber. The loading means is arranged in the housing of the pressure chamber. The loading means 800 comprises an entrance chamber 801 arranged through the wall of the upper part of the housing of the pressure chamber. Further, the loading means comprises an inner lid 803, an outer lid 804, an inner hinge 808 and an outer hinge 807. The entrance chamber further comprises an inner opening 825 at one end of the entrance chamber inside the pressure chamber and outer opening 826 at another end of the entrance chamber outside the pressure chamber. The inner opening contains a groove 809, which is provided with a seal 811. Furthermore, the outer opening contains a groove 810, which is provided with a seal 812.

In FIG. 8, the inner lid is pivotally mounted to the entrance chamber by the inner hinge for covering the inner opening. Furthermore, the inner lid is arranged outside the entrance chamber. The inner hinge is arranged in the entrance chamber inside the pressure chamber. Further, the inner lid is adapted to be opened into the pressure chamber. When the inner lid is closed it is sealed against the inner opening 825. The lid can be closed tightly against the opening with aid of an actuator, for example a linear actuator. The inner lid is actuated by the first actuator. The actuators can be controlled pneumatically (not shown). The first actuator 805 is arranged inside the entrance chamber. The inner lid is supported with the first actuator 805 to the walls of the entrance chamber.

The outer lid is pivotally mounted to the entrance chamber by the outer hinge for covering the outer opening. Furthermore, the outer lid is arranged outside the entrance chamber. The outer hinge is arranged in the entrance chamber outside the housing of the pressure chamber. Further, the outer lid is adapted to be opened into a region outside the housing of the pressure chamber and the entrance chamber. When the outer lid is closed it is sealed against the outer opening 826. The outer lid can be closed tightly against the outer opening with aid of a second actuator 806. The outer lid is actuated by the second actuator. The second actuator is arranged outside the entrance chamber and the housing of the pressure chamber. The outer lid is supported with the second actuator to the walls of the entrance chamber.

Hinges 807, 808 and actuators 805, 806 are supported only to wall of the entrance chamber. This way the movement of the housing 706, 707 does not affect the sealings of the lids 803, 804.

Both lids 803, 804 are bigger in their physical size than the inner and the outer openings 825, 826 and adapted so that the lids are sealed against the openings of the entrance chamber when the lids are pivoted in closed positions. In an open position the inner lid is pivoted into the pressure chamber. Furthermore, in an open position the outer lid is pivoted outwards from the entrance chamber, as is shown by arrows in FIG. 8.

For loading a wafer to be tested, the chuck is positioned with the positioning device near the entrance chamber. The pressure chamber is then vented, which takes a time depending on the volume of the pressure chamber. Once the pressure chamber is vented the lids 803, 804 are opened with the first and the second actuators 805, 806 respectively. The wafer is transported into the pressure chamber through the inner and the outer openings of the entrance chamber and inserted into the chuck inside the housing of the pressure chamber. Then the lids are closed with the actuators and sealed against the openings 825, 826. Advantageously both lids 803, 804 are kept open at the same time. This way the wafer can be transported into the pressure chamber without stopping between the lids 803, 804.

The loading means of the pressure testing apparatus may be automated using for example a manually or automatically operated robot, which robot is capable of moving the wafer along x- and y-axes of a Cartesian coordinate system and inserting the wafer into the chuck inside the pressure chamber. Loading of the wafer may also be done manually, for example with gripping tongs or suction equipments.

To further seal the entrance chamber, low pressure may be applied into the entrance chamber before pressurizing the pressure chamber. Thus the inner and outer lids 803, 804 are both arranged to open outwards from the entrance chamber, more easily tightened against the sealed openings. It is possible that the actuators are used at least mainly only to open the lids 803, 804. The sealing of the lids 803, 804 can be arranged to take place at least mainly with keeping a suitable pressure difference between the two sides of each lid.

In pressure testing, if there is a low pressure inside the pressure chamber the outer lid is hermetically sealed tightly against the outer opening of the entrance chamber. When there is an overpressure inside the pressure chamber the inner lid is hermetically sealed tightly against the inner opening of the entrance chamber.

The loading means of FIGS. 7 and 8 could be used on other kind of pressure testing apparatuses than the one presented in FIGS. 7 and 8.

It should be noted that a person skilled in the art might modify the pressure testing apparatus by using movable testing means, such as probes and probe card, instead of using a positioning device. Thereby, the mechanics and the chuck could be held in place if the testing means were moved. Further, instead of arranging grooves in the upper and lower part of the housing, the grooves may be arranged in the support plate. Thus the seals may also be arranged in the support plate. Although the present invention utilizes O-ring seals 510, 511, the various types of seals may be used.

While the invention has been shown and described with reference to certain embodiments thereof, these are merely provided to illustrate the invention and should not construed as limitations of the invention's scope. Thus, it will be understood by those skilled in the art that various modifications in the form and details can be made therein without departing from the spirit and scope of the invention.

The invention claimed is:

1. A pressure testing apparatus for chips on a wafer, the apparatus comprising:
   a pressure chamber comprising a housing having an upper part and a lower part;
   a support plate arranged between the upper and lower parts of the housing;
   a plurality of fasteners which extend through the support plate, the upper part, and the lower part, and fasten the upper part to the support plate, and the lower part to the support plate;
   a wafer chuck;
   a testing means; and
   a positioning device for positioning the wafer chuck and the chips relative to the testing means, wherein the wafer chuck, the testing means and the positioning device are supported to the support plate and arranged inside the pressure chamber, and wherein portions of the support plate define an opening inside the pressure chamber which provides a gas connection between the upper and lower parts of the housing.

2. The pressure testing apparatus of claim 1, wherein the support plate is arranged to cover a collar around a periphery of the pressure chamber.

3. The pressure testing apparatus of claim 1, wherein the support plate is arranged to divide the housing of the pressure chamber into the upper part and the lower part.

4. The pressure testing apparatus of claim 1, wherein the support plate extends from inside of the housing of the pressure chamber to a distance outside of the housing of the pressure chamber.

5. The pressure testing apparatus of claim 1, wherein the opening covers a part of the support plate inside the pressure chamber.

6. The pressure testing apparatus of claim 1, wherein the testing means comprises a probe card.

7. The pressure testing apparatus of claim 6, wherein the testing means comprises a card support arranged to support the probe card.

8. The pressure testing apparatus of claim 6, further comprising a vision system supported to the support plate.

9. The pressure testing apparatus of claim 1, further comprising a window arranged in the housing of the pressure chamber.

10. The pressure testing apparatus of claim 1 further comprising a loading means for transporting the wafer through the housing into and out from the pressure chamber.

11. A method of pressure testing chips on a wafer comprising the step of using the apparatus of claim 1 to test chips on a wafer.

12. The method of claim 11 wherein the chips tested are gas sensors.

13. A method for pressure testing chips on a wafer in a pressure chamber, the pressure chamber comprising a housing having an upper part and a lower part, the method comprising:
   inserting a wafer into a wafer chuck;
   positioning the wafer chuck relative to a testing means with a positioning device for positioning the wafer chuck and the chips relative to the testing means;
   supporting the testing means by a support plate;
   changing pressure inside the housing of the pressure chamber;
   moving the housing of the pressure chamber due to the pressure change;
   testing the chips on the wafer in the pressure chamber with the testing means, wherein the method further comprises:
   supporting the wafer chuck and the positioning device by the support plate;

arranging the testing means and the positioning device inside the housing of the pressure chamber;

providing an opening and thereby a gas connection through the support plate between an upper chamber and a lower chamber;

supporting and fastening with a plurality of fasteners which extend through the support plate, the upper part of the housing on the upper side of the support plate and the lower part of the housing on the lower side of the support plate, thus providing the upper chamber and the lower chamber; and applying equal pressure against the upper and lower surface of the support plate.

14. The method for pressure testing of claim 13, wherein the method comprises exerting moving force caused by the movement of the housing of the pressure chamber due to the pressure change to the wafer chuck, the testing means and the positioning device only via the support plate.

15. The method of pressure testing of claim 13 wherein the step of inserting a wafer into a wafer chuck further comprises transporting the wafer through the housing with a loading means for transporting the wafer through the housing into and out from the pressure chamber.

16. A pressure testing apparatus for chips on a wafer, the apparatus comprising:

a housing upper part;

a housing lower part;

a support plate arranged between and fastened by a plurality of fasteners to the upper and lower parts of the housing, wherein the plurality of fasteners extend through the support plate, the housing upper part and lower part defining a pressure chamber therein, the support plate extending into said pressure chamber, wherein portions of the support plate define an opening inside the pressure chamber which provides a gas connection between the housing upper part and the housing lower part;

a resealable port extending into the pressure chamber for the introduction and removal of wafers from the pressure chamber; and a wafer chuck, a chip tester, and a positioning device for positioning the chuck and the chips relative to the testing means supported to the support plate and arranged inside the pressure chamber.

17. The pressure testing apparatus of claim 16 further comprising:

portions of the housing upper part which define a plurality of first holes positioned exterior to the pressure chamber;

portions of the support plate which define a plurality of second holes positioned exterior to the pressure chamber, and aligned with the first holes;

portions of the housing lower part which define a plurality of third holes positioned exterior to the pressure chamber, and aligned with the second holes; and wherein each fastener of the plurality of fasteners extends through a first hole, a second hole, and a third hole to secure the housing upper part, the support plate, and the housing lower part together.

18. The pressure testing apparatus of claim 17 wherein the holes through which a fastener extends are of at least a first diameter which is greater than a diameter of said fastener, such that the fasteners fasten the housing upper part firmly to the housing lower part, but allow limited movement of the housing in relation to the support plate.

19. The pressure testing apparatus of claim 1 further comprising:

portions of the housing upper part which define a plurality of first holes positioned exterior to the pressure chamber;

portions of the support plate which define a plurality of second holes positioned exterior to the pressure chamber, and aligned with the first holes;

portions of the housing lower part which define a plurality of third holes positioned exterior to the pressure chamber, and aligned with the second holes; and wherein each fastener of the plurality of fasteners extends through a first hole, a second hole, and a third hole to secure the housing upper part, the support plate, and the housing lower part together.

20. The pressure testing apparatus of claim 19 wherein the holes through which a fastener extends are of at least a first diameter which is greater than a diameter of said fastener, such that the fasteners fasten the housing upper part firmly to the housing lower part, but allow limited movement of the housing in relation to the support plate.

* * * * *